US007998168B2

(12) United States Patent
Kleimann, Sr.

(10) Patent No.: US 7,998,168 B2
(45) Date of Patent: Aug. 16, 2011

(54) DRAIN TUBE STRIPPER

(76) Inventor: Robert C. Kleimann, Sr., Columbus, TX (US)

( * ) Notice: Subject to any disclaimer, the term of this patent is extended or adjusted under 35 U.S.C. 154(b) by 197 days.

(21) Appl. No.: 12/436,403

(22) Filed: May 22, 2009

(65) Prior Publication Data

US 2010/0294378 A1 Nov. 25, 2010

(51) Int. Cl.
*A61B 17/00* (2006.01)
*F16K 7/04* (2006.01)
*B08B 3/00* (2006.01)

(52) U.S. Cl. .......................... 606/209; 137/15.04; 251/6

(58) Field of Classification Search .......... 222/101-102, 222/407; 251/6-10, 4; 417/476; 294/118, 294/902; 24/115 L; 72/199, 211; 81/424.5; D24/143; 604/214, 250, 246, 249, 157, 158; 606/209
See application file for complete search history.

(56) References Cited

U.S. PATENT DOCUMENTS 1,760,467 A * 5/1930 Asher ............................. 72/211
2,197,310 A * 4/1940 Lincoln .......................... 27/21.1
2,245,030 A 7/1940 Gottesfeld et al.
2,565,646 A * 8/1951 Boyer et al. .................... 72/217
2,690,858 A * 10/1954 Peralta et al. ................... 222/93
3,194,452 A 7/1965 Sanderford
3,233,784 A * 2/1966 Gordon ........................... 222/98
3,539,081 A * 11/1970 Norton et al. .............. 222/185.1
3,625,472 A 12/1971 Rychlik
3,648,701 A 3/1972 Botts
3,788,427 A * 1/1974 Fox et al. .................. 184/105.3
4,091,815 A * 5/1978 Larsen .......................... 606/158
4,164,223 A 8/1979 Munib
4,287,890 A 9/1981 Fogarty
4,452,244 A 6/1984 Chin
4,588,159 A * 5/1986 Kawai et al. ...................... 251/4
D296,361 S * 6/1988 Gerich et al. ................ D24/143
4,819,636 A * 4/1989 Gerich et al. ................. 606/122
4,825,676 A * 5/1989 Diggins .......................... 72/211
4,944,485 A * 7/1990 Daoud et al. ...................... 251/9
5,881,916 A * 3/1999 Madjarac ...................... 222/102
6,464,710 B1 * 10/2002 Foster .......................... 606/158
7,309,055 B1 12/2007 Spiegel et al.
2004/0267305 A1 * 12/2004 Borgman ...................... 606/209
* cited by examiner

*Primary Examiner* — Gary Jackson
*Assistant Examiner* — Amy Shipley
(74) *Attorney, Agent, or Firm* — David McEwing

(57) ABSTRACT

A drain tube stripper containing two handles pivotally joined at one end. The second end of each handle contains a roller. The rollers meet when the handles are pressed together. The handles are of unequal length. A drain tube, e.g., surgical drain, can be stripped of fluid and material buildup by placing the open rollers over the tube and pressing the handles together. The rollers thereby pinch the drain tube and the rollers allow the device to be moved along the drain tube pushing fluid and material ahead of the rollers. The drain tube stripper allows the tube to enter between the rollers from the side and exit from the side of the opposing handle. The tube drain stripper may also contain a guide component to minimize entanglement of the drain and the device is rolled along the drain tubing.

12 Claims, 6 Drawing Sheets

DRAIN TUBE STRIPPER

BACKGROUND OF INVENTION

1. Field of Use

The device subject of this disclosure is a hand held device with rollers that can pinch a flexible drain tube and push liquid and other debris through the tube to a collection bag or similar device. It is particularly suited for clearing surgical drain lines.

2. Prior Art

Related devices are disclosed in the prior art, including devices that have two arms attached together at one end and a complementary set of rollers at the second end. See for example patent application US 2004/0267305 of Mark H. Borgman filed Jun. 30, 2003.

SUMMARY OF INVENTION

The invention comprises a drain tube stripper. The stripper is comprised of two handles of unequal length. At the first end of each handle are a complementary set of rollers. The unequal handle length may allow one roller to fit in the same longitudinal axis as the second roller when the pivotally adjustable handles are closed together. Each roller is mounted on the first end of each handle. The second end of each handle is pivotally joined together.

When the handles are open, a gap is formed between the rollers and the flexible tube can enter between the rollers from one handle side and pass through the second handle side unobstructed. The opening of the handle can be facilitated by a spring mechanism or similar compressible and expandable device placed between the handles.

The handles are mounted perpendicular to the pivot axis. This can allow the handle arms to nest adjacent to each other when the pivot attachment is closed, thereby allowing the rollers to lie in the same axis of orientation and make the tube stripper more compact for storage.

SUMMARY OF DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

DETAILED DESCRIPTION OF INVENTION

Figure 2:
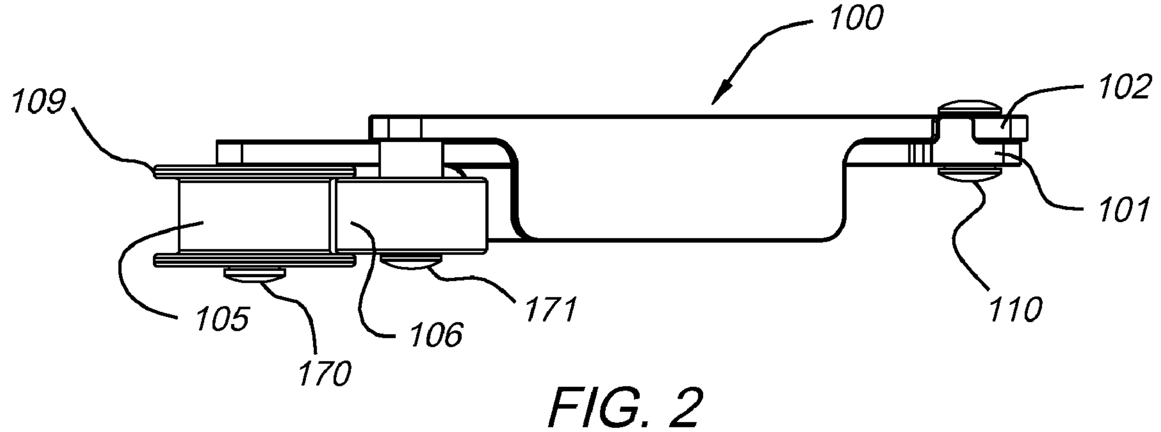
FIG. 2 illustrates a top view of the device showing the relative positions of the rollers when the handles are closed.

The invention subject of this disclosure includes, but is not limited to, the following novel features. The two sets of rollers each attached to a handle are offset from the other by the unequal length of the handles. This allows the rollers to nest in series or in line when the device is completely closed, i.e., the pivot attachment is folded against itself. See FIG. 2 illustrating the device 100 and the nested two rollers 105, 106 mounted on axles 170, 171 and the opposite second handle ends 101, 102 pivotally attached 110. The handles are in a parallel axis of orientation.

Figure 1:
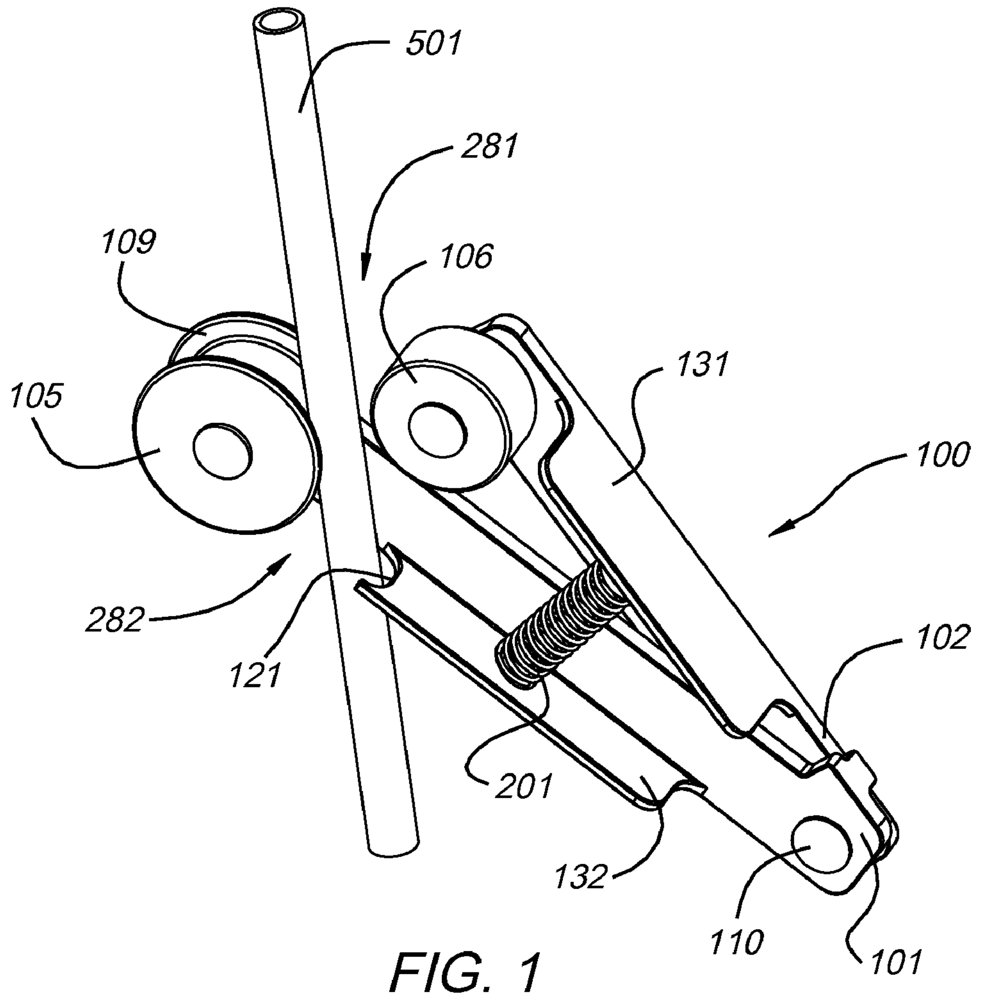
FIG. 1 illustrates the device of the invention showing the two arms of unequal length and pivotally attached and showing the position of the flexible tube positioned between the rollers.

FIG. 1 is a perspective illustration of the device 100. The unequal length of the handles allows the flexible tube to enter from one side 281 of the device. The tube 501 is pinched between the two sets of rollers and the tube exits from the second side 282 of the handle configuration. It will be appreciated that this pathway is in contrast to prior art methods wherein the tube enters through the front between the rollers.

Figure 3:
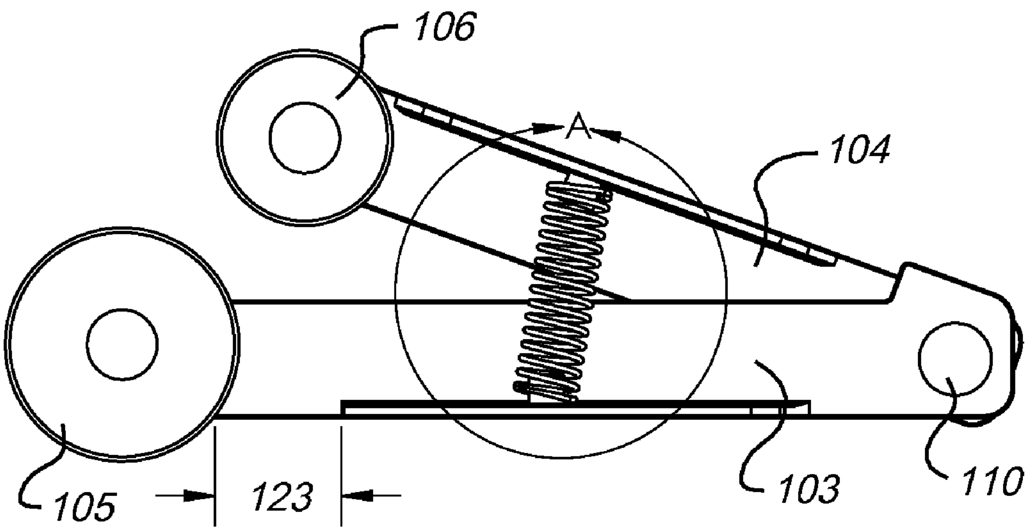
FIG. 3 is a side view of the device with handles open and the spring device used to push the handles open. The gap between flanged roller and the guide component is illustrated.

The perspective illustration of FIG. 1 shows optional hand grip 132 attached to the first handle 103 and the hand grip 131 attached to the second handle 104 illustrated in FIG. 3. The hand grip 132 forms a tube guide 121 proximate to the tube exit point 282. Also illustrated is the juncture of the first handle end 101, and second handle end 102 and pivot component 110. The tube holding flange 109, a component of the first roller 105, is also illustrated. The drain tube 501 is placed between the rollers 105, 106 and the guide 121.

Figure 5:
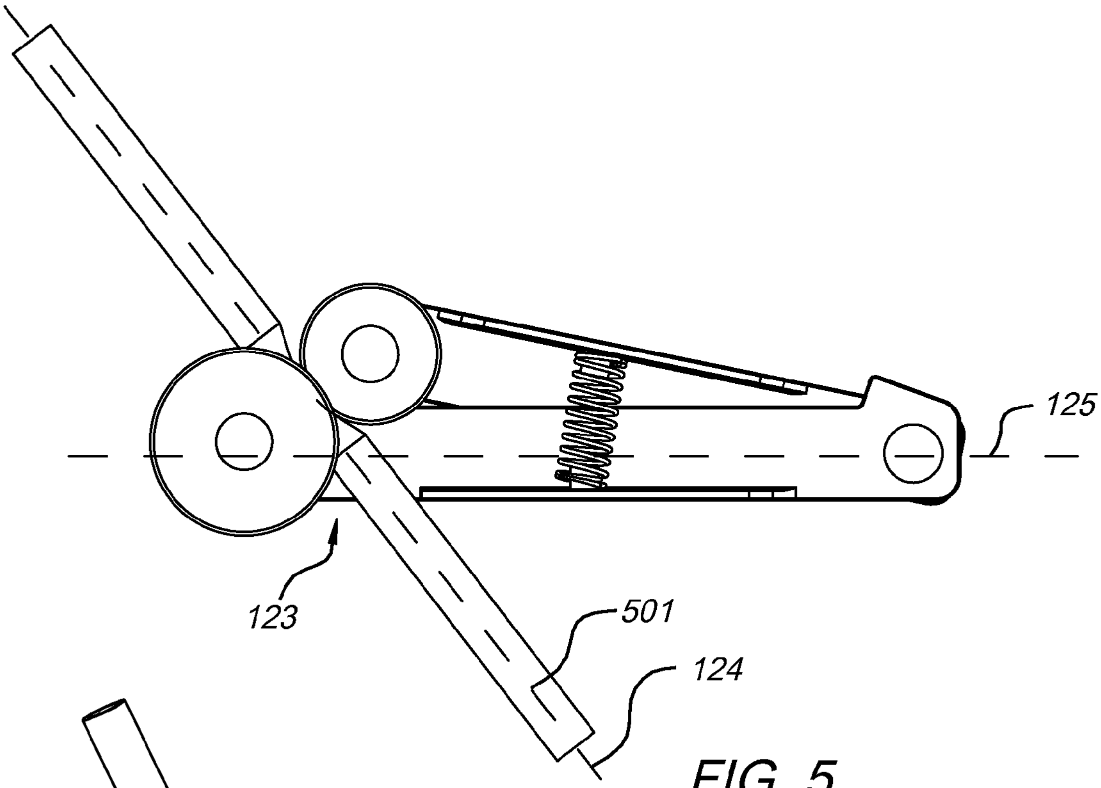
FIG. 5 illustrates a side view of the rollers pinching the tubing. The tubing enters between the top of the device between the rollers and exits the device within the gap between the guide component and the flanged wheel.

See FIG. 5 illustrating the gap 123 between the first roller 105 and the end of the handgrip 132 attached to the first handle. This gap 123 forms part of an angled pathway 124 separately oriented to the longitudinal orientation 125 of the handles 103, 104. When the handles are not closed, a gap exists between the two rollers. This creates a pathway through which the flexible tube can pass from one side of the device to the other side. See FIG. 1.

Figure 6:
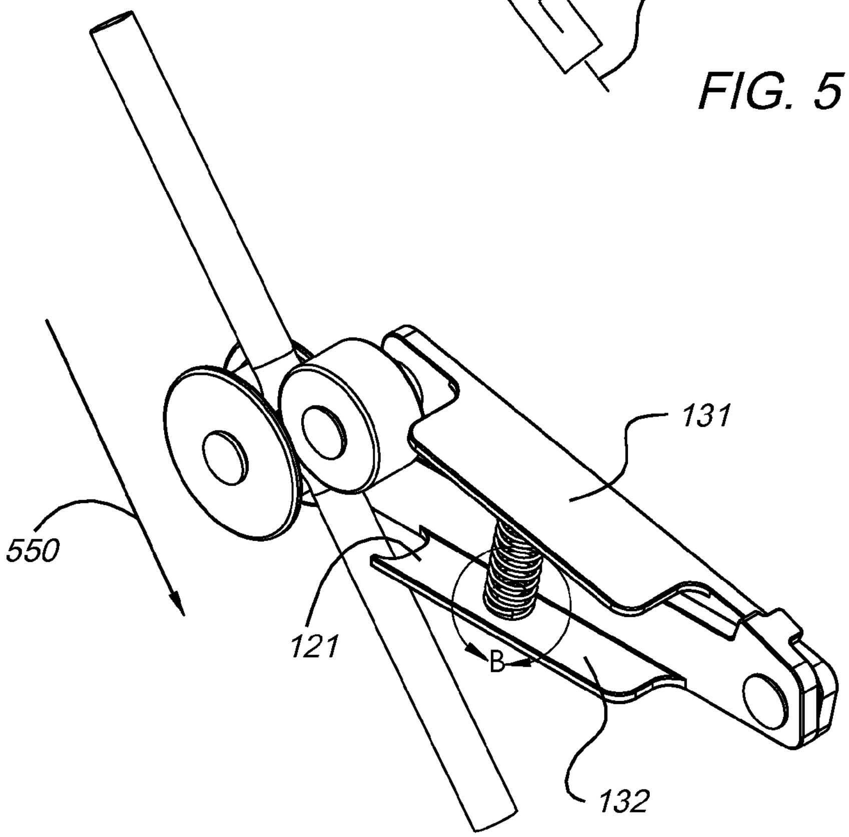
FIG. 6 is a perspective view of the tube pinched between the rollers.
Figure 8:
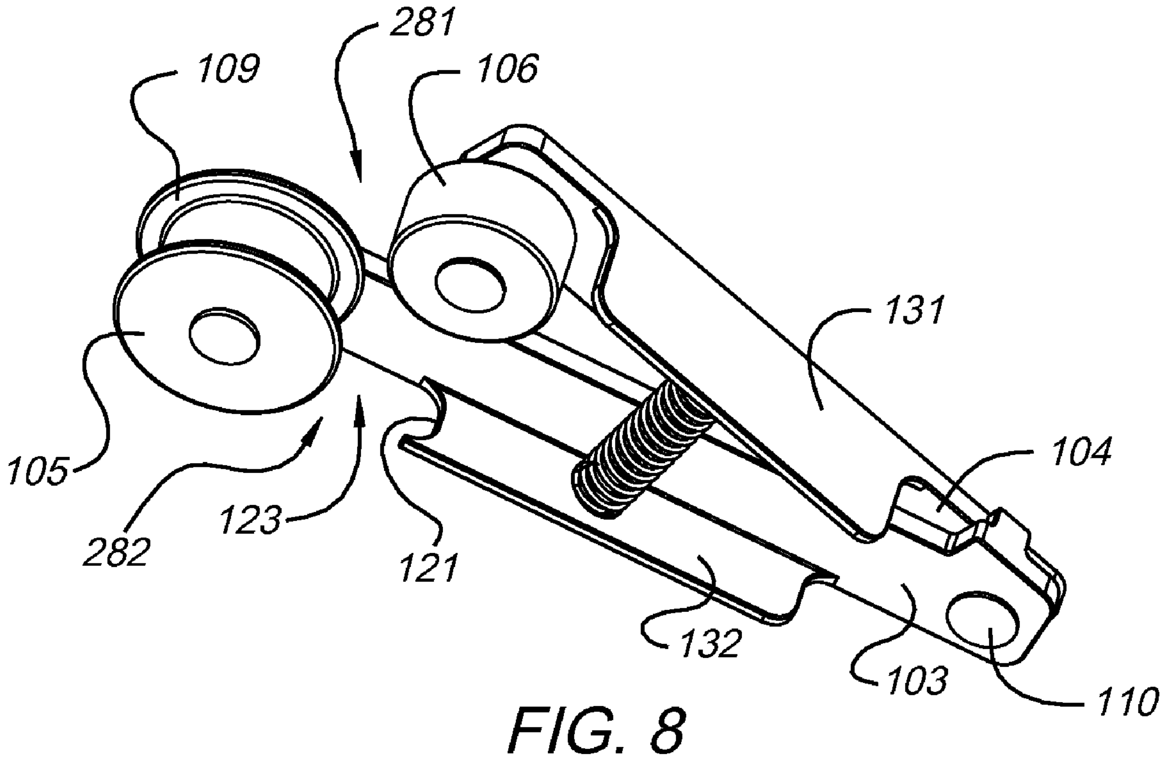
FIG. 8 illustrates perspective view of the rollers and handle device.

A guide component guides the path of the tube section through the first handle side. This prevents the tube from tangling with the handle, pivoting mechanism, etc. This is important in view of the squeezing action of the device on the tube while the device is simultaneously moved down the tube to a drain bag or similar device. See FIG. 8 illustrating the gap 123 between the roller and the first handle grip 132. The handles 103, 104 have a scissor-like configuration thereby allowing the handles to accommodate pressure without out breaking or bending. The guide component 121 is shown in FIGS. 6 and 8. The curved surface of the guide component is illustrated in FIGS. 1 and 8. This curved surface facilitates placement of the round drain tubing within the guide component.

Figure 4:
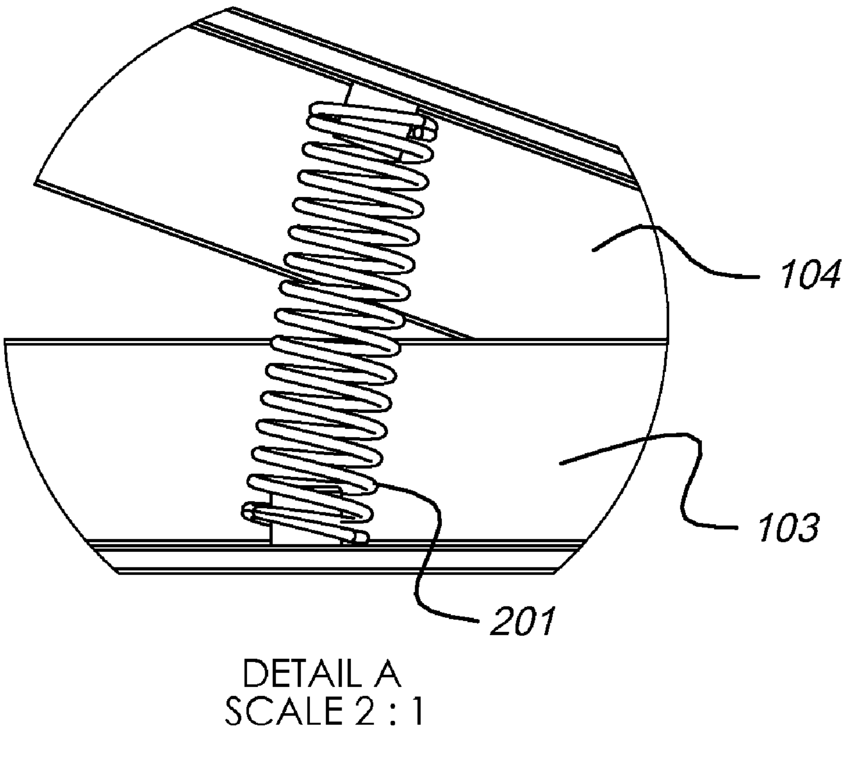
FIG. 4 is a detailed view of the spring component that can be used in one embodiment of the invention. Also illustrated is the position of the handles perpendicular to the axis of orientation of the pivot.

FIG. 4 illustrates an embodiment comprising a top and bottom attachment of a spring 201 to each handle. The sides of the handles 103, 104 are also shown (mounted perpendicularly to the pivot axis).

Also illustrated in FIG. 5 is the flexible tube pinched between rollers 105, 106. Note the two handles are not parallel. This is because the drain tube occupies space between the rollers thereby preventing the rollers from completely closing. The spacing between the rollers is assisted by the recoil force of the compressed spring. The handles of the stripper are pushed together by a user's hand (not shown). It will be appreciated that the invention is not limited to a particular spring structure or spring location.

FIG. 6 is a perspective view of the device and also illustrates the flexible tube 501 protruding from a first side 131 of the device and continuing from the second side 132. The device, pinching the tube, is pulled over the tube in the direction shown by vector arrow 550.

Figure 7:
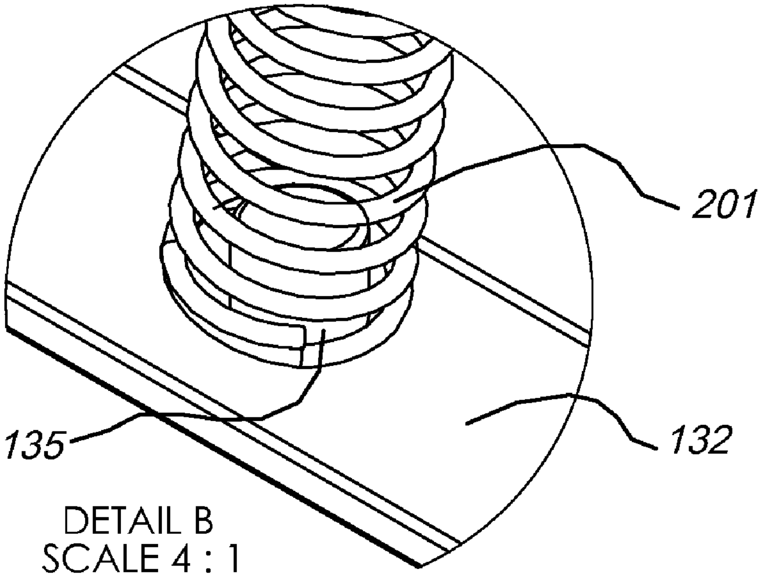
FIG. 7 is a detailed perspective view of the attachment mechanism of the spring to the hand grip component.

FIG. 7 also illustrates one embodiment for attaching the spring 201 to the handle grip 132. The handle grip contains a protrusion 135 holding one end of the spring. A matching protrusion can be installed on the other handle grip. Alternative methods of spring attachment include a protruding tab with an eyelet through which the spring can be tied or threaded.

FIG. 8 is a perspective view of the device and illustrating the first roller 105 with the flange 109 and the second roller 106 wherein the width of the wheel 106 fits within the width of the flange 109. This relationship is also illustrated in FIG. 2.

It will be appreciated that the positioning of each roller may be reversed, e.g., the first roller 105 may be mounted on the shorter second handle 104 and the second roller 106 mounted on the long first handle 103. Also illustrated is the gap 123 between the roller 105 and the curved guide 121. The flexible tube may fit within the curved surface of this guide 121. Also illustrated is the gap 281 commencing on the first side and extending 282 from the first roller 105. Also illustrated is the end of the shorter handle 104 and the end of the longer handle 103, joined together by a pivot or hinge mechanism 110.

Figure 9:
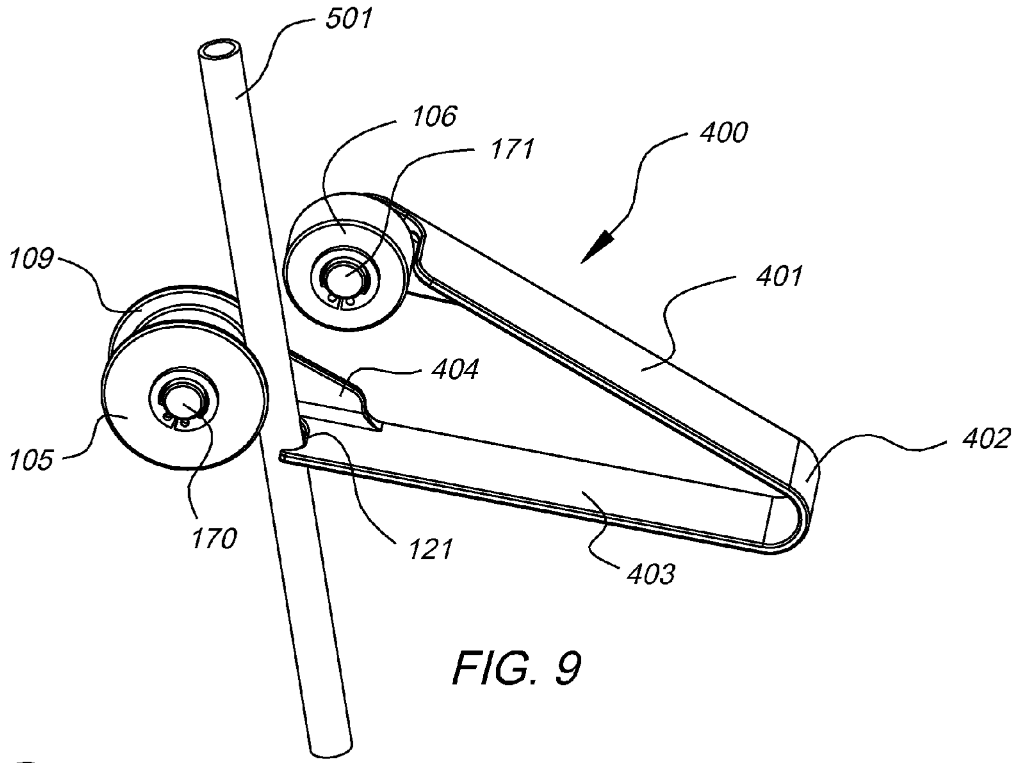
FIG. 9 illustrates a different embodiment of the invention where the two handles are not pushed apart by a spring but by the flexible component joining the two handles. The handles can be squeezed close with one roller meeting the other roller.

FIGS. 9 through 12 illustrate another embodiment 400 of the invention. In this embodiment, the handles 401, 403 are flat in contrast to the scissor-like position of the handles 102, 103 illustrated in FIG. 3. The second handle 401 and the first handle 403 are joined by a single piece elbow component 402. The elbow component can be compressed when the handles are pushed together but returns to its original shape when the pushing force is removed. In the original shape, the first roller 105 and second roller 106 are separated or open. FIG. 9 illustrates the device in an open position. It will be appreciated that the single piece design is more sanitary than a multi-piece hinged or pivot design. The handles and elbow component can be easily wiped clean.

Also illustrated in FIG. 9 is the curved guide component 121. Also illustrated are the two rollers 105, 106 and the flange component 109. The axle 170, 171 of each roller is illustrated. The reinforcing component 404 connecting the handle 105 to the roller axle 170 is also illustrated. Also illustrated is the tubing 501 positioned within the flange component 109 of roller 105 and the guide 121.

It will be appreciated that the invention is not limited to the illustrated roller configuration. For example a roller may have a concave surface and used in conjunction with a complementary roller with a convex surface.

It will be further appreciated that the embodiment of the invention comprising straight handles of unequal length can be closed with the handles and rollers in the same axis of orientation. This saves storage space.

Figure 10:
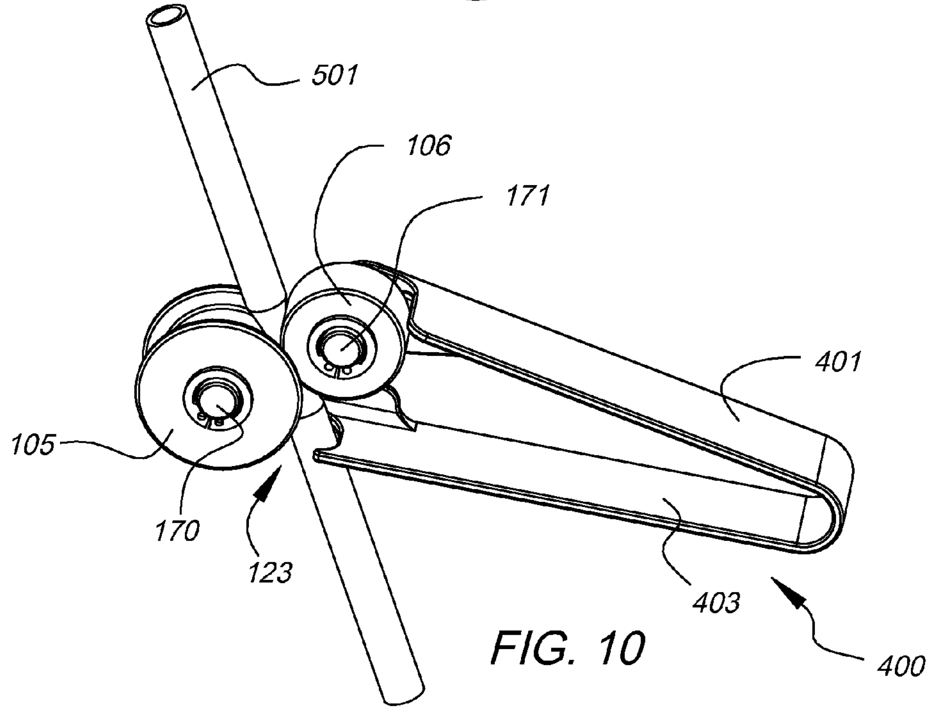
FIG. 10 illustrates a second embodiment with the handles squeezed together and the two rollers pinching a tube.

FIG. 10 is a perspective view of the device containing the tube 501 wherein the device is in a closed position. The handles 401, 403 are squeezed together. This squeezing action pinches the tube between the first roller 105 and the second roller 106. The rollers rotate on the axles 170, 171 as the device is pulled along the tube thereby pushing any liquid or debris.

Figure 11:
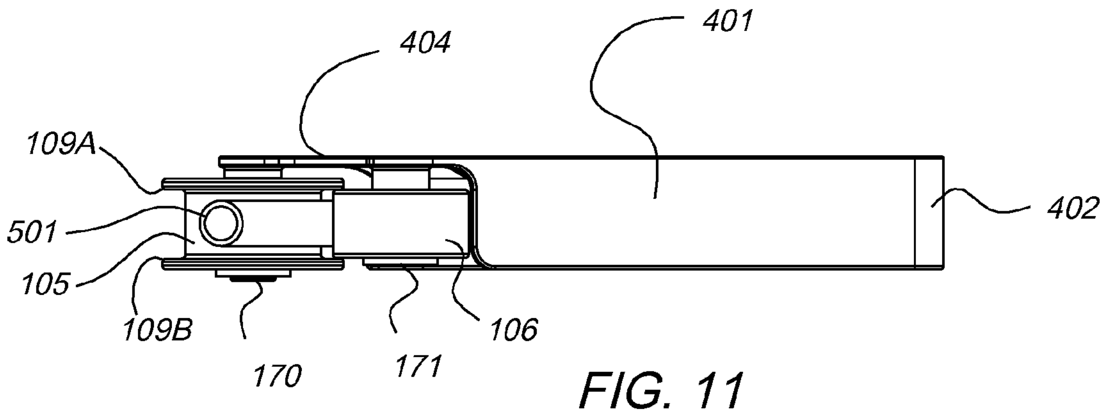
FIG. 11 illustrates a top view of the invention with the first roller fitting close to the flanged roller.

FIG. 11 is a top view of the device illustrating the top second handle 401, the second roller 106, a section of tubing 501 pinched between the second roller and the first flanged 109A, 109B roller 105. It will be appreciated that in another embodiment, the first roller 105 may have only a single flange 109B. The tube will be held in place on the roller side by the reinforcing component 404.

Figure 12:
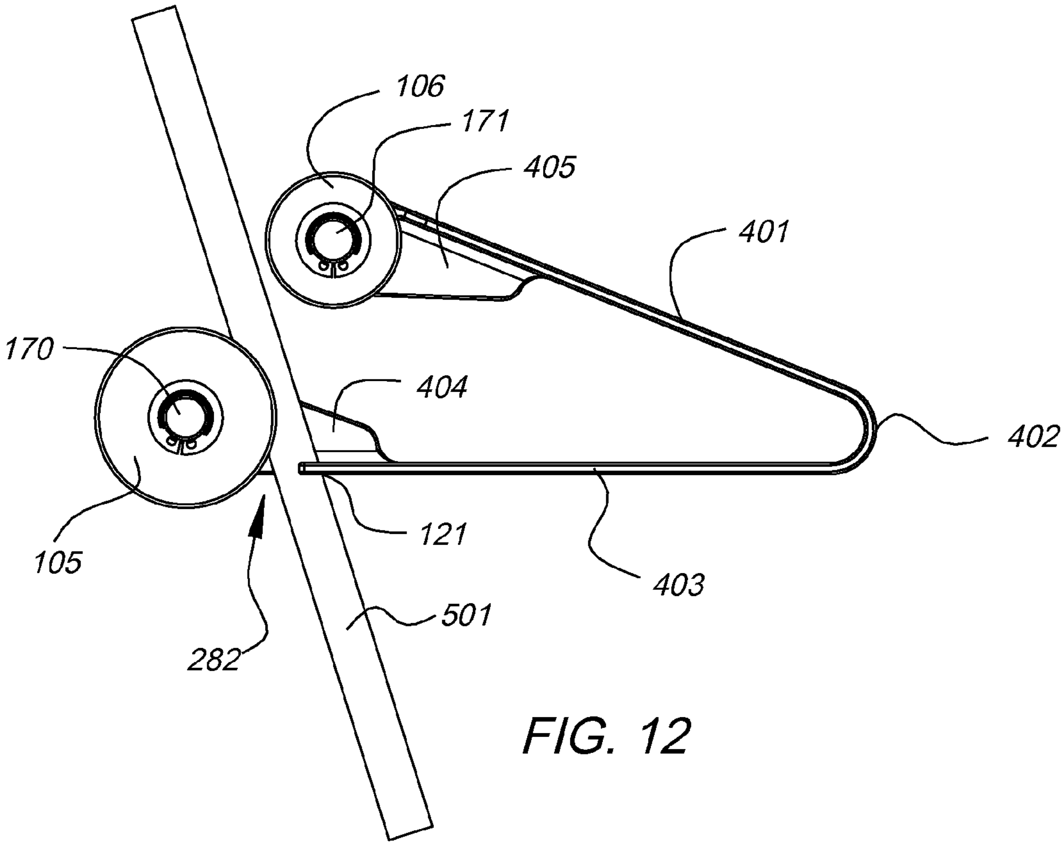
FIG. 12 illustrates a side view of the invention with the handles and rollers open.

FIG. 12 is a side view of the device with a section of tubing 501 positioned between the first roller 105 and the guide component 121 comprising part of the first handle 403. Also shown is the second roller 106, the attaching reinforcement mechanism 405 attaching the axle 171 of the second roller 106 to the second handle 401 and the elbow connecting component 402. The axle of the first roller is also shown 170.

The device subject of this invention may be made from metal such as stainless steel or spring steel. The device may also be made from plastics such as ABS plastic, nylon, polyoxymethylene (Delrin) and acrylic. The device can be made using injection molding or vacuum molding.

This specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention may be utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

I claim:

1. Drain tube stripper comprising:

a) first and second handles of unequal length wherein each handle has a first end and a second end and the second ends are connected with a closeable hinge having a pivoting axis;

b) the first end of the first handle and the first end of the second handle each contain a roller that presses with a roller of the other first handle end when the handles are closed;

c) the handles are oriented perpendicular to the pivoting hinge;

d) a gap exists between the rollers when the handles are open e) the axis of each roller is parallel to the pivoting axis;

f) one handle comprises a guide component extending laterally outward from the lower handle and mounted on the side of the handle having a front curved surface that engages a drain tube after the drain tube passes through the rollers.

2. The drain tube stripper of claim 1 further comprising rollers fitting together wherein one first roller has a two flanges mounted on each side of the roller and the second roller fits within the space between the flanges of the first roller to hold a drain tube in place between the rollers when the handles are closed.

3. The tube stripper of claim 1 comprising the handles containing one or more guide components.

4. The tube stripper of claim 1 further comprising a first and second handle each perpendicularly oriented to the hinge axis of rotation.

5. The tube stripper of claim 1 further comprising a spring.

6. The tube stripper of claim 1 wherein the handle comprises a hand grip component.

7. The tube stripper of claim 6 further comprising the hand grip component comprising a guide component that guides the drain tube from the rollers of the first and second handle to pass underneath a handle.

8. Drain tube stripper comprising a) a first long handle and a second short handle wherein a second end of each handle is joined together by a spring like elbow that permits the rollers on the first end of each handle to be squeezed together so that one roller contacts the other roller and when the squeezing force is released, a gap forms between the rollers; and b) one handle comprises a guide flange with a curved surface.

9. The drain tube stripper of claim 8 further comprising each roller contacting the other when the handles are aligned in the same longitudinal axis of orientation.

10. A method of cleaning drain tubes using the device of claim 1, comprising the steps of:

a) opening two handles attached with a pivoting axis and wherein a first handle is longer that a second handle;

b) placing a drain tube within a gap between a roller at a first end of each handle and each roller having an axis parallel to the pivoting axis;

c) extending the tube through the rollers and past a guide component;

d) closing the handles so that the tube is pressed between the rollers and extending past the guide component and beneath one handle; and e) moving the closed tube stripper down the drain tube.

11. The method of claim 10 further comprising the step of squeezing the two handles together.

12. The method of claim 10 further comprising the following steps:

a) placing the tube stripper proximate to a patient;

b) squeezing the handle to pinch the tube between the rollers; and c) pulling the tube stripper along the tube away from the patient.

* * * * *